United States Patent [19]

Wannlund

[11] Patent Number: 5,159,197
[45] Date of Patent: * Oct. 27, 1992

[54] LUMINESCENCE TEST AND EXPOSURE APPARATUS

[75] Inventor: Jon C. Wannlund, Carlsbad, Calif.

[73] Assignee: Difco Laboratories, Detroit, Mich.

[*] Notice: The portion of the term of this patent subsequent to Jan. 15, 2008 has been disclaimed.

[21] Appl. No.: 567,383

[22] Filed: Aug. 14, 1990

Related U.S. Application Data

[62] Division of Ser. No. 155,955, Feb. 16, 1988, Pat. No. 5,035,866.

[51] Int. Cl.$^5$ .............................................. G01N 21/76
[52] U.S. Cl. ...................... 250/328; 250/361 C; 422/52; 422/102
[58] Field of Search .................. 250/361 C, 328, 526; 422/52, 102

[56] References Cited

U.S. PATENT DOCUMENTS

| | | | |
|---|---|---|---|
| 3,785,928 | 1/1974 | Kessler | 422/102 |
| 4,895,706 | 1/1990 | Root et al. | 422/102 |
| 4,985,631 | 1/1991 | Wannlund et al. | 250/361 R |

FOREIGN PATENT DOCUMENTS 207532 1/1987 European Pat. Off. ........ 250/361 C Primary Examiner—Carolyn E. Fields
Attorney, Agent, or Firm—Gregory Garmong

[57] ABSTRACT

Apparatus for performing and measuring chemical reactions includes a reaction test apparatus having reaction wells wherein reactants are controllably mixed, and exposure apparatus which receives and positions the reaction test apparatus adjacent a photographic film. Each of the reaction wells includes at least two reaction cups, arranged one above the other. The uppermost reaction cups have orifices in the bottoms, so that liquid can be mixed and reacted in the uppermost cup, and then controllably transferred to the lower cup to be mixed with additional reactants. In a preferred embodiment, the reaction cups are supported in plates that are structurally integrated with the cups, and are superimposed to make a test block. The test block is retained in the exposure apparatus, and liquid is forced from the upper cup to the lower cup by application of pressure to the top of the upper cup. The apparatus of the invention is particularly suited for measuring reactions that produce luminescence of short duration, as the reactants can be conveniently mixed in darkness, while the film is being exposed.

7 Claims, 6 Drawing Sheets

LUMINESCENCE TEST AND EXPOSURE APPARATUS

This is a division of application Ser. No. 07/155,955, filed Feb. 16, 1988, now U.S. Pat. No. 5,035,866.

BACKGROUND OF THE INVENTION

This invention deals with apparatus for performing chemical reactions, and, more particularly, with self-contained reaction apparatus for performing a sequential set of chemical reactions, and monitoring the final results.

In several types of chemical and medical test procedures, a liquid such as a body fluid must be reacted with individual reactants in a sequence of related but separate chemical reactions, and then the final product analyzed. Traditionally, such procedures have been performed by placing the fluid into a reaction tube or the like, adding the remaining reactants for the first reaction, and permitting the first reaction to proceed to completion. The further reactants for the second reaction are added, and the second reaction is permitted to proceed to completion. This stepwise operation can be repeated as many times as necessary, until a final reaction product is obtained. The final reaction product is then analyzed by the appropriate technique.

This approach to performing laboratory procedures requires considerable technical expertise by the person performing the test, since reactants must be carefully measured and added at the correct times. Moreover, if any of the reactants are perishable or deteriorate with time, the person performing the testing must exercise a critical judgment as to whether the reactants are suitable for performing the test at that time. Because these types of expertise must usually be specially taught, it is not always possible to use such testing procedures at rural or remote locations, as the necessary trained personnel, reactants, and facilities are not available.

Certain types of testing procedures do not lend themselves to such wet chemical techniques. One example is a test procedure wherein the final reaction product is analyzed by a luminescence reaction. In this type of procedure, the amount of a final product is indicated by the amount of light produced in a light producing reaction, one of whose reactants is the final product of one or more prior reactions. In certain types of luminescent reactions, the light is produced within a few seconds after the reactants are mixed together. If the traditional wet chemical procedure is used, the luminescent reactants must be mixed with the final reaction product and placed within a photometer or camera that measures the light, and the light detection initiated, within no more than about two seconds, or much of the resulting light is not measured and is lost. As is apparent, attempting to add precise amounts of reactants and perform the light measurement under such time pressures is difficult, and often leads to a mistake that requires the test to be repeated. Sometimes the mistake cannot be readily detected, and erroneous results are reported. Better techniques are therefore required to utilize sequential procedures where a final product is detected with a luminescent reaction.

An example of such a testing procedure is the detection of harmful bacteria in the urine of persons by luminescence, termed a bacteriuria test. For many years, the presence of bacteria in urine has been determined by culturing experiments which take at least 24 to 48 hours to perform and may yield inaccurate results. Culturing procedures are also costly, and often cannot be accomplished at remote locations.

More recently, a testing procedure has been developed whereby the presence of bacteriuria is detected more quickly, utilizing luminescent tagging of reaction products. In such a procedure, bacteria in urine are detected by releasing the chemical adenosine triphosphate, also termed ATP, from the bacteria. The available ATP reacts with bioluminescent reactants to produce light, and the amount of light measured indicates the concentration of bacteria initially present. ATP can also be present from other, non-bacterial sources, and any such extraneous ATP is first removed from the system, before releasing the bacterial ATP. Thus, there is a first chemical reaction whereby the extraneous ATP present from all non-bacterial sources is eliminated, a second, separate chemical reaction whereby the bacterial ATP is released into solution, and finally a third reaction of the light producing reactants with the released bacterial ATP. The second and third reactions can be performed simultaneously, but the first reaction must be completed before the bacterial ATP is released. This test is direct and reliable, and relatively inexpensive.

The luminescent test for bacteriuria can be performed by conventional wet chemical procedures such as previously described, but in this form suffers from many of the drawbacks discussed earlier, and in addition must be performed in darkness so that the production of light can be measured. An automatic luminometer testing apparatus has also been developed, which permits all of the reactions to be conducted within a single analytical luminescence apparatus, and yields a quantitative measure of the bacteriuria present in the urine of a patient. This approach has significantly advanced the art of bacteriuria testing.

The luminometer testing apparatus, however, costs several thousand dollars to purchase. Its use in some circumstances, such as rural and undeveloped areas, is therefore limited. The chemicals used in the luminometer are perishable. Additionally, in many instances the use of the luminometer provides much more information than is necessary. For example, in most cases urine samples yield negative bacteriuria results. The quantitative analysis capability of the luminometer is not required as to those negative results. Furthermore, it is generally observed that positively testing patients are usually heavily positive, and there are few cases of borderline results where the urine specimen contains a bacteriuria count near the arbitrarily defined dividing line between positive and negative results. The proper treatment is often identical for all positively testing persons. That is, in the majority of instances a simple qualitative determination of negative or positive bacteriuria count in a specimen is sufficient for screening purposes, and in many cases it is sufficient for all diagnostic purposes. In the event that further quantitative study is required, then the luminometer at a central location could be used more efficiently than for general screening studies.

There is therefore a need for an apparatus and test protocol for performing qualitative or semi-quantitative tests for bacteriuria by the luminescent analysis procedure. The apparatus must permit controlled sequential chemical reactions, and specifically must permit removal of non-bacterial ATP prior to the release of bacterial ATP for luminescent detection. The apparatus should be sufficiently simple that it can be used by technicians with little training, should serve to minimize errors due to chemical deterioration or technician error, and should be inexpensive so that tests can be performed economically. The present invention fulfills this need, and further provides related advantages.

SUMMARY OF THE INVENTION

The present invention is embodied in apparatus and a process for testing specimens requiring sequential chemical reactions, using light-producing reactions to indicate the presence of a selected reactant. The luminescence is recorded on photographic film for further analysis. The apparatus is fully self contained so that the testing can be accomplished in a lighted room, can be operated with little training, minimizes the chances of error, and is economical to construct and use. With a preferred embodiment of the apparatus having multiple test wells, either one or multiple tests can be performed, and the remaining unused wells can be utilized at a later time. The apparatus thus provides excellent flexibility of use, and is adapted for use either in a busy laboratory or at remote sites.

Practice of the invention involves two separate but interrelated pieces of apparatus. The chemical reactions are performed within a reaction test apparatus, which in turn is contained within an exposure apparatus which controls the operation of the reaction test apparatus and records the light output.

In accordance with the invention, a reaction test apparatus for testing a specimen therein comprises a plurality of test wells, each of said test wells including a lower reaction cup having a final reactant therein, and an upper reaction cup positioned above the lower reaction cup and having a penultimate reactant therein, the upper reaction cup further having an orifice in the bottom thereof disposed such that liquid flowing through the orifice is discharged into the lower reaction cup; and a support for the test wells and the reaction cups thereof, the support including an upper plate supporting the upper reaction cups, and a lower plate supporting the lower reaction cups, the upper and lower plates being keyed to register said upper and lower reaction cups for each of said test wells.

More generally, a reaction test apparatus for testing a liquid placed therein comprises at least one test well, the test well having therein a lower reaction cup having a final reactant therein, an upper reaction cup positioned above the lower reaction cup and having a penultimate reactant therein, the upper reaction cup further having an orifice in the bottom thereof disposed such that liquid flowing through said orifice is discharged into the lower reaction cup, so that a pressure applied to the top of the upper reaction cup forces liquid contained in the upper reaction cup downwardly through the orifice into the lower reaction cup; and a support for the test well and the cups thereof.

As indicated, the presently preferred utilization of the reaction test apparatus is in analyzing for the presence of particular reactants by luminescence emitted during chemical reactions. In accordance with another aspect of the invention, luminescene exposure apparatus for conducting luminescene reaction tests on specimens contained within test wells in a reaction test apparatus comprises a lower housing having a flat upwardly facing internal surface for receiving a piece of film thereupon, a fixed shutter covering the upwardly facing surface and having a plurality of openings therethrough positioned to correspond to the locations of the test wells in the reaction test apparatus, biasing means on the fixed shutter for resisting the downward movement of the reaction test apparatus, when the reaction test apparatus is placed upon the fixed shutter, and a movable shutter between the internal surface and the fixed shutter; and an upper housing including translation means for controllably urging the reaction test apparatus downwardly against the resistance of the biasing means, thereby contacting the bottoms of the reaction wells in the reaction test apparatus with the piece of film in the lower housing, and pressure application means for applying a pressure to the top of the reaction wells in the reaction test apparatus responsive to a force applied externally to the exposure apparatus, the upper housing and the lower housing being adapted to fit together so as to exclude light from the interior thereof.

The reaction test apparatus permits the penultimate, or next to last, chemical reaction to be accomplished in the upper test cup of each reaction well. When the penultimate chemical reaction is complete, the reactants are forced through the orifice in the bottom of the upper test cup into the lower test cup. In the lower test cup, the reaction products from the completed penultimate chemical reaction are reacted with the final reactants, to produce final reaction products. These final reaction products are then measured by an appropriate technique.

In the preferred bioluminescent bacteriuria analysis, a urine specimen is added to the upper reaction cup containing reactants to release non-bacterial ATP into solution and to eliminate the non-bacterial ATP from solution. This release and elimination reaction typically requires about 10 to 60 minutes to complete. The urine treated to completion in the upper reaction cup, containing only ATP within bacteria, then is forced to the lower reaction cup through the orifice in the upper reaction cup. It is necessary that the elimination of non-bacterial ATP be completed before beginning the reaction in the lower reaction cup, or erroneous results will be obtained. In the lower reaction cup the bacterial ATP is released and reacted with light-producing reagents which react with free ATP to create luminescence in an amount related to the presence of bacterial ATP in the original sample, a reaction typically requiring only about 30 seconds.

The exposure apparatus of the invention is designed to cooperate with the reaction test apparatus in accomplishing the sequential reactions and the measurement of the light emitted. The lower housing of the exposure apparatus receives a piece of film to be exposed to the light of the luminescene reaction. Preferably, the film is instant developing film, so that the results of the testing can be seen within one minute or less of completion of the exposure.

The lower housing includes the fixed shutter that covers the film, but has fixed openings therethrough corresponding to the positions of the reaction wells in the reaction test apparatus. The fixed shutter preferably includes a plurality of collars that extend upwardly and over the downwardly projecting test wells, to position the test wells and prevent light produced by a reaction in one test well from finding its way onto the portion of the film below another test well. The biasing means, such as a coil spring or a leaf spring, projects upwardly from the fixed shutter, to resist the downward movement of the reaction test apparatus when it is placed onto the fixed shutter. The movable shutter is placed between the fixed shutter and the film, and can be selectively opened to expose the film to the light produced in the bottom cup of the test well.

The upper housing fits together with the lower housing to exclude light from the interior. A translation mechanism forces the reaction test apparatus downwardly against the resistance offered by the biasing means, into near-contact or direct contact with the film. A pressure application means within the upper housing permits the application of an externally controllable pressure to the top of each test well, as through a shaped rubber or elastic diaphragm contacting and fitting over the top of each of the upper cups in a preferred embodiment. The diaphragms, one for each test well in the reaction test apparatus therein, are attached to a diaphragm support, with a pressure bar portion extending externally of the upper housing. Application of a downward force on the pressure bar applies a pressure to the interior of the upper cup of each test well, forcing any liquid therein downwardly through the upper orifice into the lower test well. When the liquid from the upper test cell enters the lower cup, it reacts with the chemicals therein, and almost immediately produces light.

In operation of the exposure apparatus, the upper housing is first opened and the reaction test apparatus placed upon the fixed shutter of the lower housing. The placement is easy and natural to perform, as the downwardly projecting test wells of the reaction test apparatus fit easily into the upwardly projecting collars of the fixed shutter. The biasing spring on the fixed shutter prevents the reaction test apparatus from sitting in direct contact with the movable shutter that is between the fixed shutter and the film, so that the movable shutter can be readily moved at a later time.

The upper housing is then closed, and the movable shutter pulled out to expose the film to the bottoms of the test wells. The translation mechanism is operated to force the reaction test apparatus downwardly to contact the bottoms of the test wells directly to the film. Next, the pressure bar is pressed to force liquid from the upper reaction cup to the lower reaction cup, whereupon the luminescence reaction proceeds and the resulting light is recorded on the film. After this light producing reaction is judged to be substantially complete, usually about 30 seconds, the translation mechanism is operated to release the downward force on the reaction test apparatus, so that it rises under the force of the biasing means and is no longer in contact with the film. The movable shutter is closed, and the upper housing is opened to remove the reaction test apparatus. The film is developed, either before or after the upper housing is opened, and the process is complete. The exposure apparatus is then ready for another test.

A key feature of the present invention is the presence of the orifices in the bottom of each upper reaction cup. These orifices can be sealed with a small amount of nonreactive silicone laboratory grease prior to use to fully plug the orifices. The downward pressure of the rubber diaphragm forces the grease from the orifice, so that the liquid can pass therethrough into the lower reaction cup.

In a typical use of a preferred form of the invention for performing a number of bacteriuria tests, the laboratory technician is furnished with a reaction test apparatus having a foil cover over the tops of the reaction wells, to prevent contamination. In the most preferred form of the invention, 12 reaction wells are provided in the reaction test apparatus. The technician removes the foil cover from enough of the test wells to accomodate the number of urine specimens to be tested and adds the urine samples to the upper reaction cup of each of the respective wells. The urine samples are permitted to remain in the upper reaction cups for a period of time sufficient to complete the reaction of release and elimination of non-bacterial ATP, typically about 10 to 60 minutes. During this period, the reaction test apparatus may be placed within the exposure apparatus, or may remain on the laboratory bench, as this reaction within the upper reaction cups need not be conducted in darkness.

After completion of the reaction period in the upper test cup, the reaction test apparatus is placed onto the fixed shutter of the lower housing of the exposure apparatus, if this was not done previously. The exposure apparatus is then operated in the manner previously described. Upon operation of the pressure bar, the urine solution is forced from the upper reaction cup to the lower reaction cup through the orifice. The urine solution then reacts with the remaining reactants in the lower reaction cup, and light is produced if bacteriuria are present. The light is recorded on the film as a direct measure of the presence of bacteria in the initial urine specimen. The presence of bacteriuria is detected by an exposed bright spot on the film. If there are any unused test wells in the reaction test apparatus, these are recognized by their remaining foil seal, and can be later used in testing of other urine specimens.

A feature of the preferred embodiment of the present invention is the provision of certain key reactants in a solid form. The apyrase enzyme and somatic release reagent packaged in the upper reaction cup are provided in a solid form, as are the light producing reactants, bacterial release reagent, bovine serum albumin, and buffering agent in the lower reaction cup. These reactants normally deteriorate in effectiveness when stored in a liquid or liquid solution form for extended periods of time. Their subsequent use may lead to error in the test results. Providing these reactants in a solid form has the important advantage of prolonging their lives in the absence of refrigeration or other means for reducing deterioration, and also eliminates the possibility of spilling. The methodology for preparing these reactants in solid form will be described subsequently.

The reaction test apparatus of the present invention can also be provided with three or more superimposed reaction cups in each test well, if additional sequential chemical reactions are to be performed prior to the light producing reaction. For example, it is known that certain urine dilutions yield higher light outputs in the luminescence reaction. To dilute the urine after the release and elimination of non-bacterial ATP is complete, another reaction cup is provided, so that the reacted urine is diluted in the additional reaction cup. The additional reaction cup also has an orifice therein, possibly with a grease plug, so that the diluted urine then flows out of the cup under the applied pressure. This dilution use of the invention sacrifices the advantage of using all-solid reactants, but it achieves the advantage of performing the desired dilution of the urine. The dilution solution can be formulated to contain only stable ingredients, so that the long term stability and storability of the reaction test apparatus are not lost. Spillage can be prevented by sealing the upper edges of the middle reaction cups with nonreactive grease to the bottoms of the upper reaction cups or their support.

It will be appreciated that the present invention provides a highly flexible system for conducting sequential chemical reactions and then measuring the results of the reactions with a light producing reaction. The apparatus is readily provided in a kit form, with the exposure apparatus being reusable indefinitely. The test can be performed by relatively inexperienced personnel, as all reactants except the test specimen are prepackaged into the reaction test apparatus. The resulting exposed film provides a permanent record of the test results, which can be evaluated either by the technician or a doctor. The testing procedure yields qualitative or semi-quantitative results particularly useful in a screening of specimens, and can be economically used in central or remote laboratory facilities with equal ease and identical results. Complete screening of specimens is often accomplished within less than an hour, so that the results are available before the patient leaves the doctor's office. Other features and advantages of the invention will be apparent from the following more detailed description, taken in conjunction with the accompanying drawings, which illustrate, by way of example, the principles of the invention.

DETAILED DESCRIPTION OF THE PREFERRED EMBODIMENT

Figure 5:
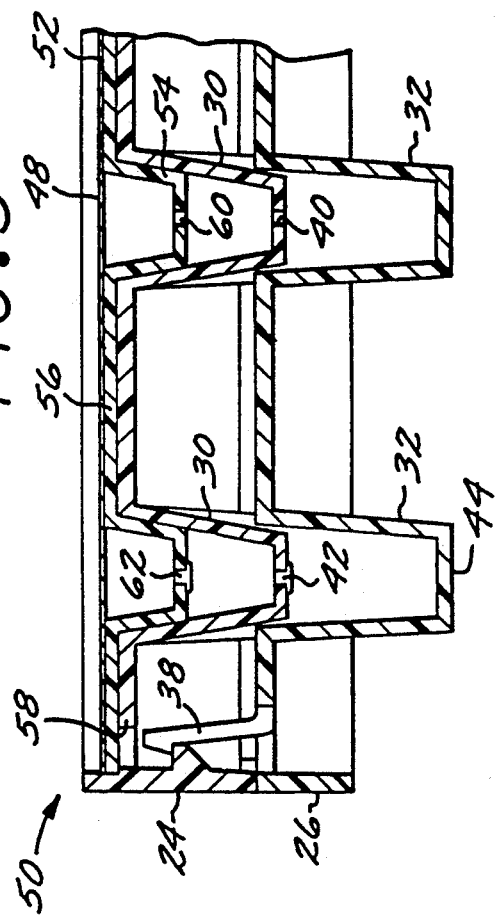
FIG. 5 is a fragmented side sectional view of a reaction test apparatus having three reaction cups in each test well.
Figure 4:
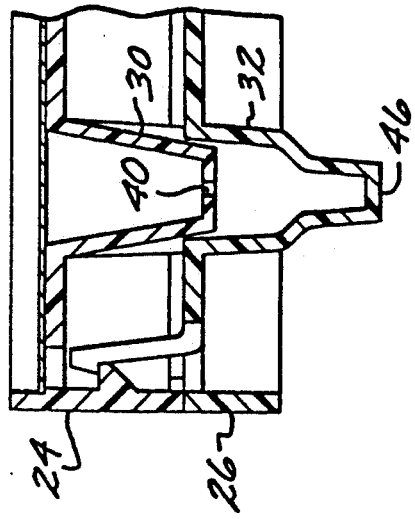
FIG. 4 is a fragmented side sectional view like that of FIG. 3, except illustrating an alternate configuration of the lower reaction cup.
Figure 6:
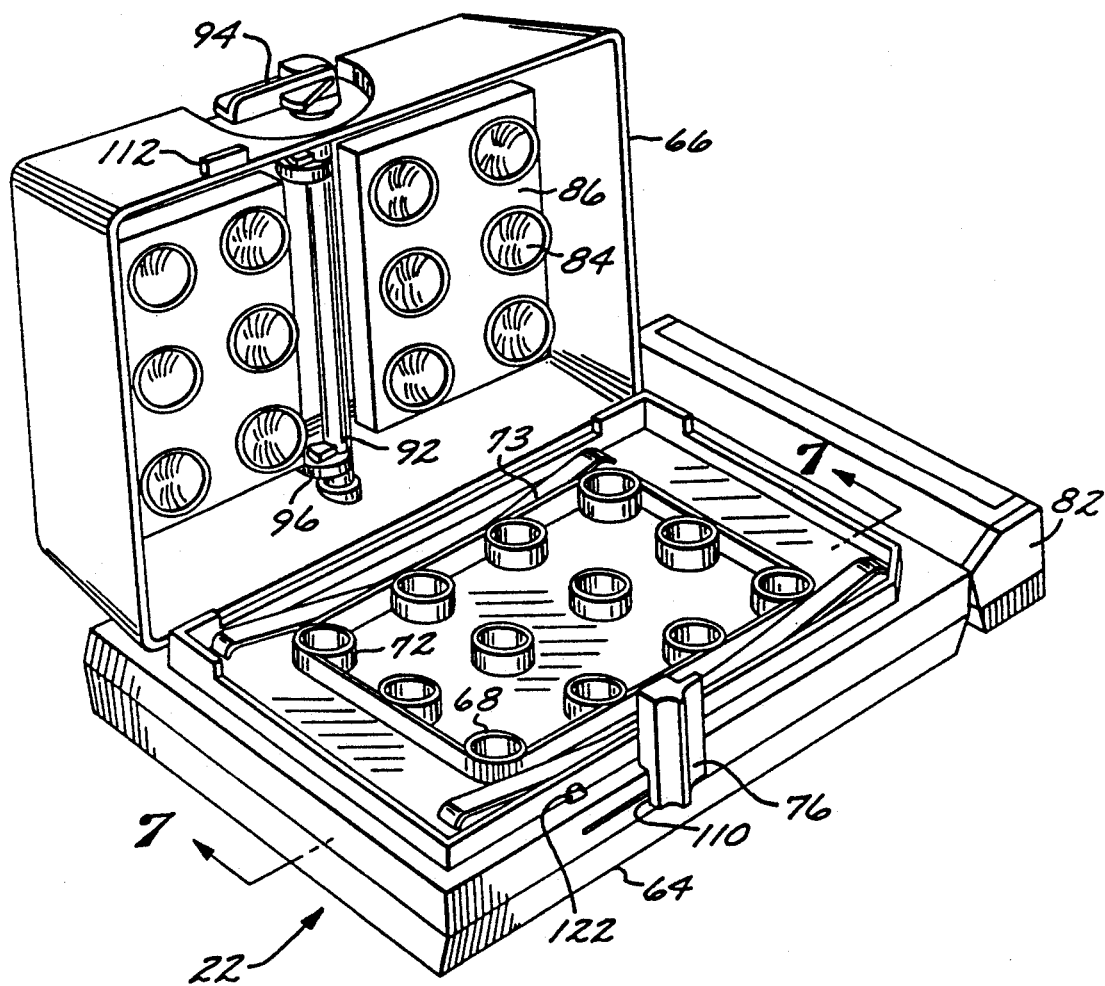
FIG. 6 is a perspective view of the exposure apparatus, opened to illustrate the interior structure.
Figure 7:
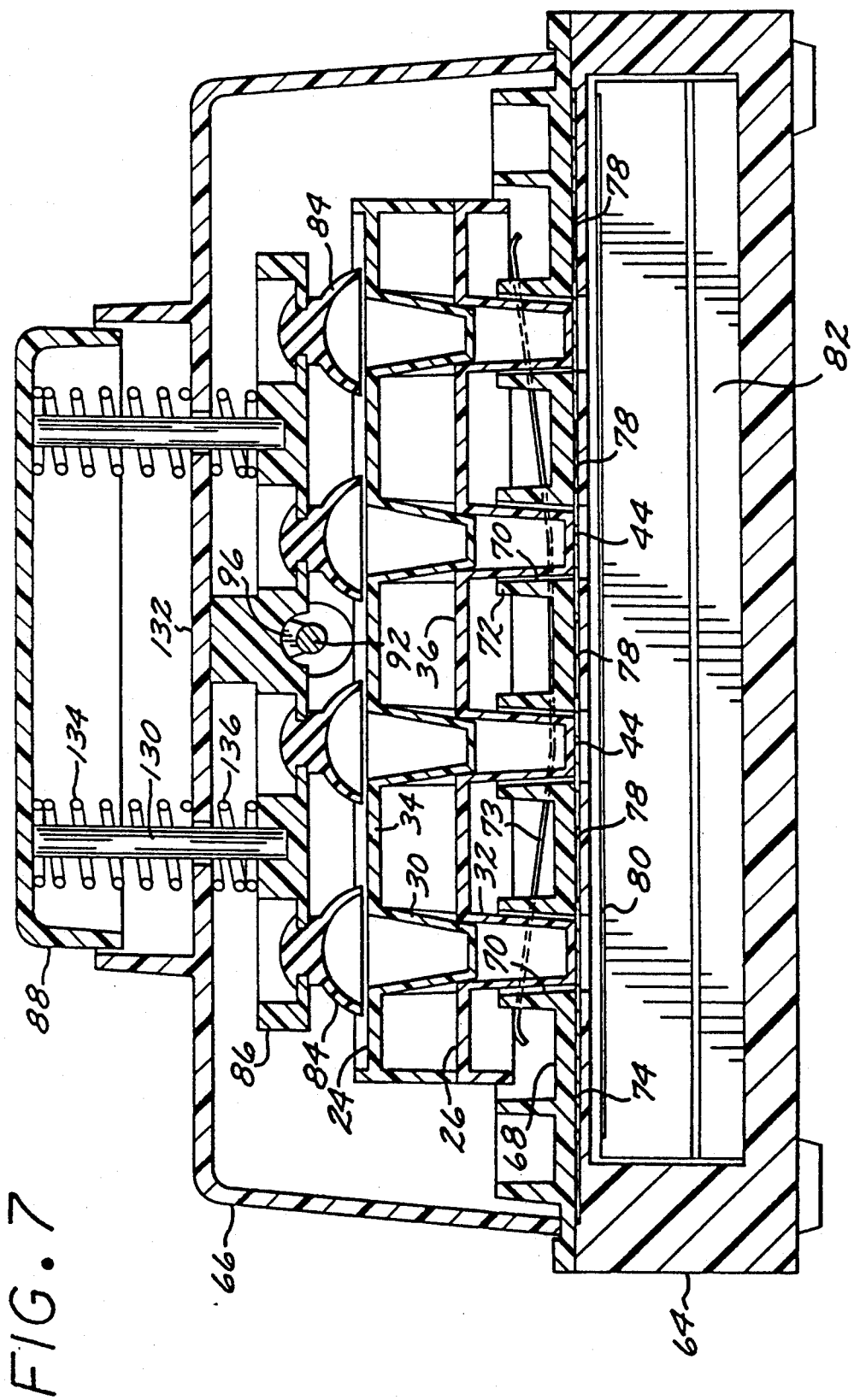
FIG. 7 is a side sectional view of the exposure apparatus of FIG. 6, taken generally along line 7—7.
Figure 8:
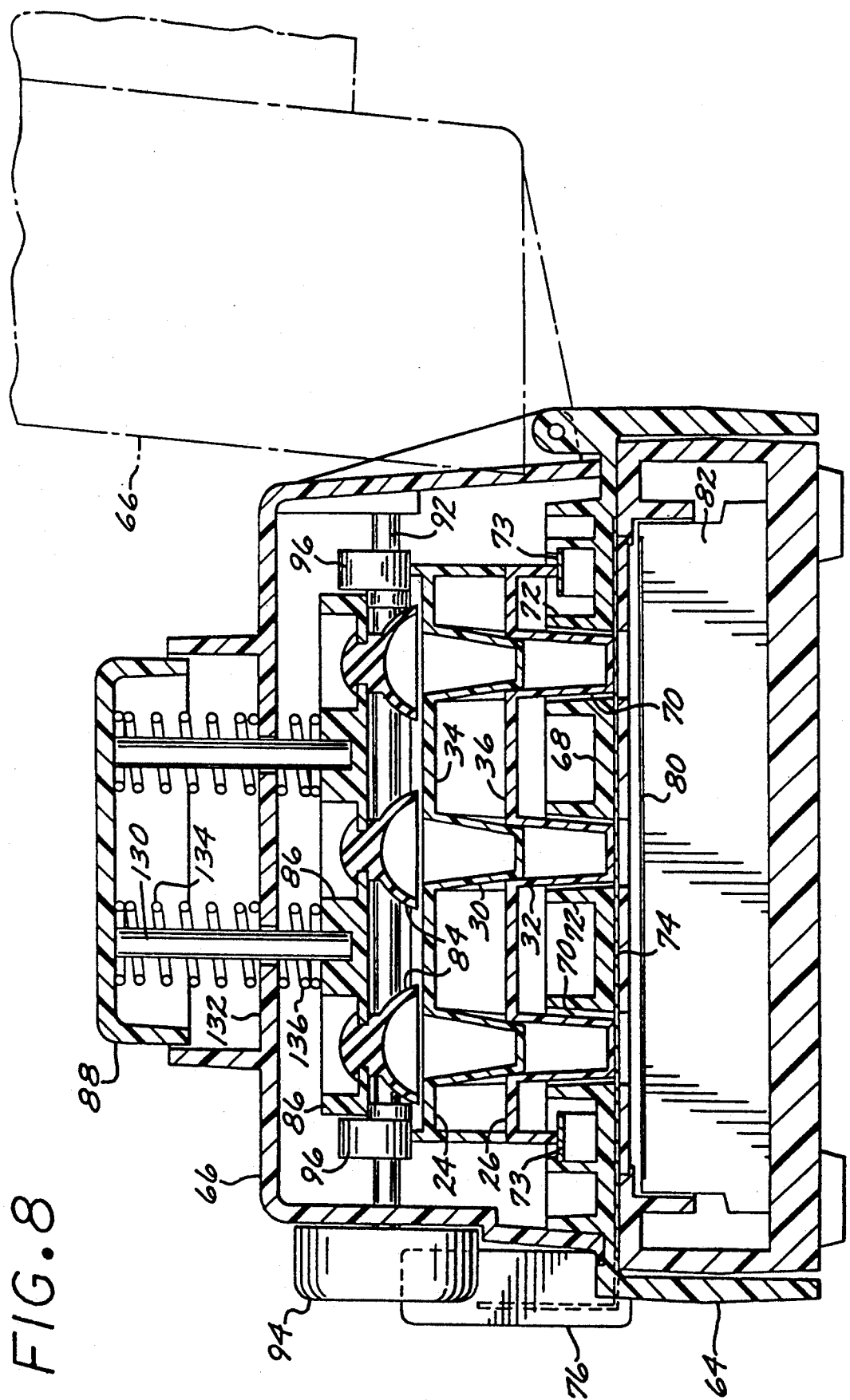
FIG. 8 is an end sectional view of the exposure apparatus.

The present invention is embodied in a reaction test apparatus 20, illustrated in FIGS. 1-5, and a cooperative exposure apparatus 22, illustrated in FIGS. 6-10. The cooperative relationship between the reaction test apparatus 20 and the exposure apparatus 22 is illustrated in FIGS. 7 and 8. As shown therein, the reaction test apparatus 20 is operated by placing it within the exposure apparatus 22, closing the exposure apparatus 22, and operating the externally extending controls of the exposure apparatus 22 to effect and record chemical reactions occurring within the reaction test apparatus 20.

Figure 1:
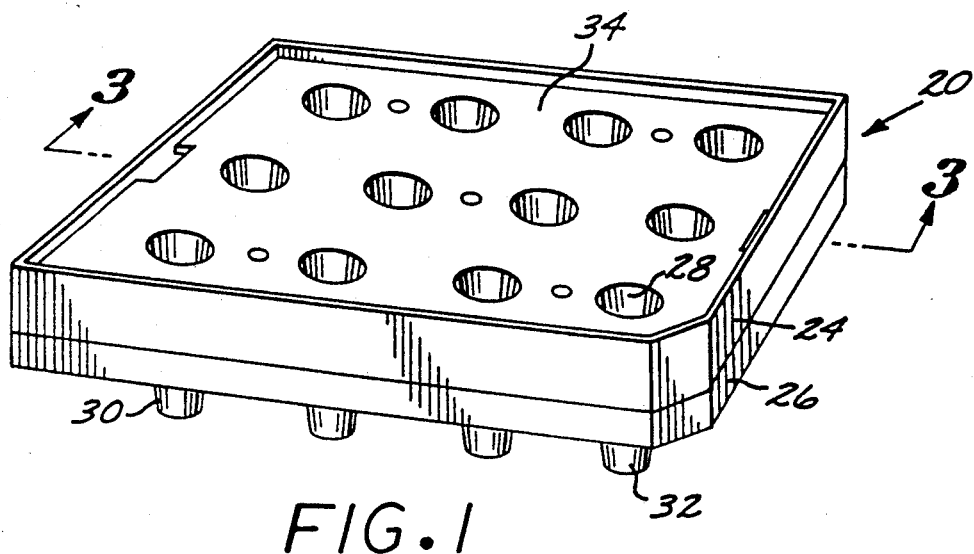
FIG. 1 is a perspective view of a reaction test apparatus.
Figure 2:
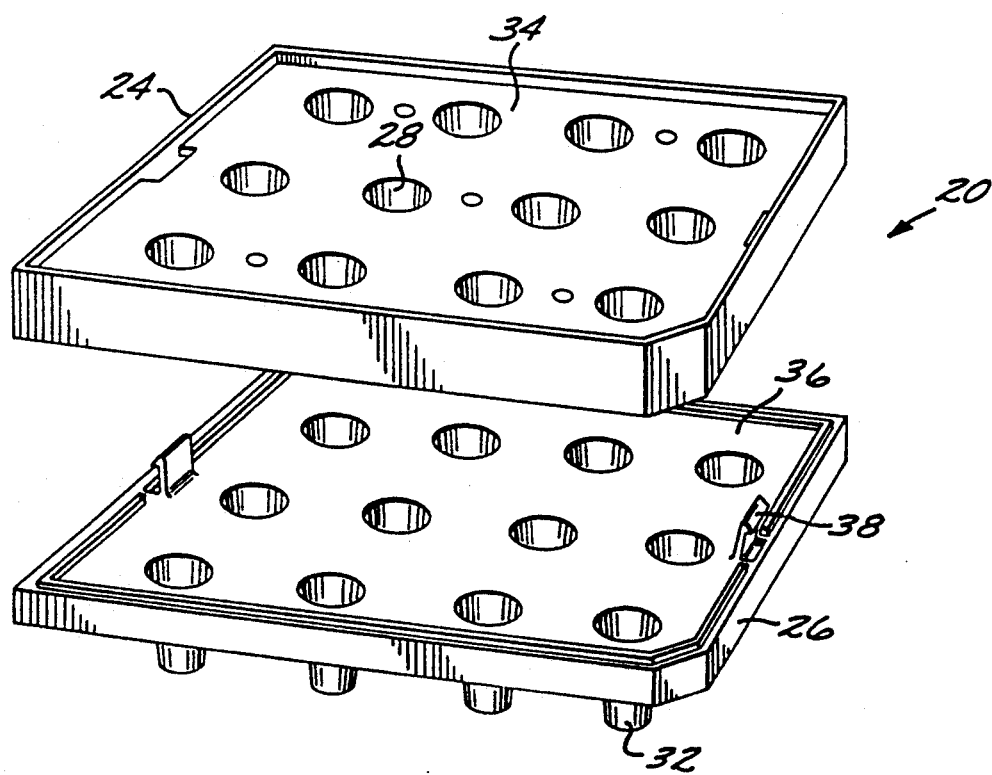
FIG. 2 is an exploded perspective view of the reaction test apparatus of FIG. 1.
Figure 3:
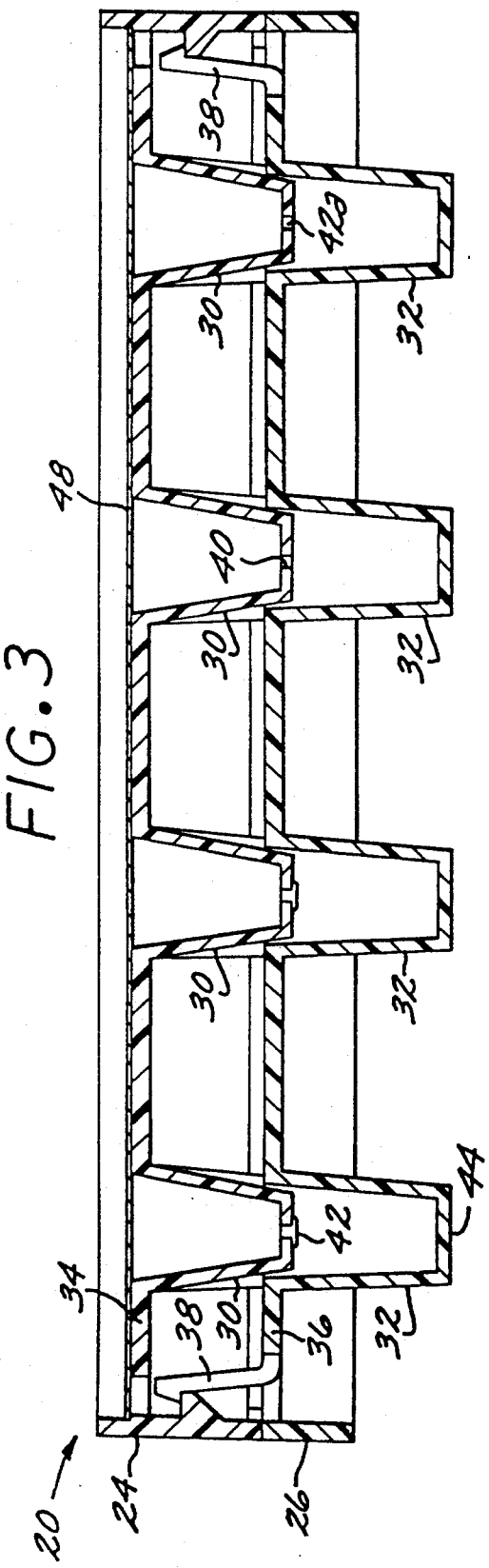
FIG. 3 is a side sectional view of the reaction test apparatus of FIG. 1, taken along line 3—3.

FIG. 1 illustrates generally the reaction test apparatus 20, while FIG. 2 illustrates the apparatus 20 in exploded view and FIG. 3 illustrates the interrelationship of the elements within the apparatus 20. The reaction test apparatus 20 includes an upper plate 24 and a lower plate 26 which include a plurality, preferably 12, of test wells 28. The upper plate 24 and the lower plate 26 are preferably each one-piece molded plastic structures, although it would be possible to use an alternate structure wherein the test wells 28 were fabricated as separated elements and pressed into bores in the plates 24 and 26.

As illustrated in FIGS. 2 and 3, each test well 28 includes an upper reaction cup 30 and a lower reaction cup 32. One upper reaction cup 30 for each test well 28 is molded into the upper plate 24, and one lower reaction cup 32 for each test well 28 is molded into the lower plate 26. The shape of the upper plate 24 is defined, and the upper reaction cups 30 are held in position, by an upper web 34 that forms the skeleton of the structure of the upper plate 24. Similarly, the shape of the lower plate 26 is defined, and the lower reaction cups 32 are held in position, by a lower web 36 that forms the skeleton of the structure of the lower plate 26.

Each cup 30 and 32 has an open top and sides that taper inwardly from the top to the bottom of the cup. The inward taper permits the upper reaction cups 30 to be nested within the lower reaction cups 32 during assembly of the reaction test apparatus 20. The two plates 24 and 26 are dimensioned to be otherwise conformable. The reaction test apparatus 20 can therefore be assembled in the manner illustrated in FIG. 2, by slipping each upper cup 30 downwardly into the corresponding lower cup 32, and then joining the upper plate 24 to the lower plate 26, either permanently or releasably.

Preferably, the plates 24 and 26 are releasably joined, as an aid in assembly of the apparatus 20. The joining mechanism includes a pair of molded catches 38, one on each end of the lower plate 26. Each catch 38 is a tab having a tapered upper end extending upwardly from the outside end of the lower web 36, and is dimensioned to be slightly flexible. The upper plate 24 is releasably secured to the lower plate 26 by slipping it downwardly into secure contact with the lower plate 26, so that the catch 38 on each end captures and snaps closed over the respective end of the upper web 34. The upper plate 24 can be disassembled from the lower plate 26, if desired, by manually pulling each catch 38 outwardly and lifting the upper plate 24 upwardly.

As more fully illustrated in FIG. 3, the upper reaction cup 30 has an orifice 40 in the bottom thereof. The orifice 40 is closed by a removable plug 42, preferably a small amount of chemically inert silicone laboratory grease. An increased internal pressure within the upper reaction cup 30, as controllably applied by the exposure apparatus 22, causes the plug 42 to be ejected. Ejection of the plug 42 opens the orifice 40, so that any liquid therein falls downwardly into the lower reaction cup 32, which is positioned directly below the upper reaction cup 30 in their nesting relationship. In some instances, surface tension of the liquid in the upper reaction cup 30 is sufficient to prevent it from flowing through the orifice 40, as illustrated at numeral 42a of FIG. 3. In those instances, no plug 42 is provided. (In FIG. 3, the two leftmost upper reaction cups 30 are illustrated with the plugs 42 in place, while the two rightmost upper reaction cups 30 are illustrated without plugs.)

The lower reaction cup 32, also illustrated in FIG. 3, has no orifice therein, but instead has a flat bottom 44 adapted to be placed in close contact with the surface of a photographic film. In another embodiment illustrated in FIG. 4, the lower wall of the lower reaction cup 32 is further tapered into a flat bottomed tubular section 46, to achieve direction of the light produced by a chemical reaction within the cup 32 into a smaller area as defined by the size of the bottom of the tubular section 46, and thereby increase its intensity within that area.

In typical use of the reaction test apparatus 20, chemical reactants are placed into the reaction cups 30 and 32 prior to shipment to customer laboratories. The preferred reactants and the method of their preparation will be described subsequently. To retain the chemical reactants in the cups 30 and 32, and to prevent their contamination, a foil cover 48 is preferably sealed over the top of the upper plate 24. In use, the foil cover 48 is removed or punctured when a particular test well 28 is used, and this physical disruption of the foil cover 48 serves as an indicator of which test wells 28 have been used.

In another embodiment illustrated in FIG. 5, a reaction test apparatus 50 contains an upper plate 24 and a lower plate 26, which are preferably identical to those previously described, and in addition a top plate 52. The top plate includes a plurality of top reaction cups 54, supported by a top web 56. The top reaction cups 54 are conformably arranged to nest with the upper reaction cups 30 in the upper plate 24. With the use of this embodiment in mind, the upper plate 24 is fabricated with an upwardly projecting lip 58. The top web 56 is dimensioned to fit snugly within the bounds of the lip 58 and be retained therein. As illustrated in FIG. 5, the top plate 52, upper plate 24, and lower plate 26 are conformably nested and retained together in the manner described.

The top reaction cup 54 has an orifice 60 in the bottom thereof similar to that in the bottom of the upper reaction cup 30, so that removal of a plug 62 from the orifice 60 allows liquid to flow out of the top reaction cup 54 into the upper reaction cup 30. The addition of the top reaction cup 54 permits another chemical reaction or procedure to be performed prior to the reaction in the upper reaction cup 30, and prior to the reaction in the lower reaction cup 32. As is apparent, the principle of multiple reaction cups can be extended to four, five, or more vertically aligned reaction cups in a single reaction test apparatus.

The reaction test apparatus 20 or 50 is preferably used in conjunction with the exposure apparatus 22 illustrated in FIGS. 6–10. As illustrated in FIG. 6, the exposure apparatus 22 includes a lower housing 64 and an upper housing 66 which is hingedly joined along one side to the lower housing 64. The hinged arrangement permits the upper housing 66 to be closed with the lower housing 64 to form a light tight container, and to be opened to insert a reaction test apparatus therein in the manner to be described.

The sectional view of FIG. 7 shows the apparatus 22 with the upper housing 66 in the closed position and a reaction test apparatus 20 in place therein. The upwardly facing portion of the lower housing 66 is a fixed shutter 68 having a plurality of openings 70 therethrough. The positions of the openings 70 are selected to correspond to the positions of the test wells 28 of the reaction test apparatus 20, so that each test well 28 is positioned directly above one of the openings 70. A collar 72 surrounds and projects upwardly from each opening 70. The collars 72 are cylindrical and have inner diameters sufficiently large that the test wells 28 fit slidably within the collars 72. The cooperative engagement between the test wells 28 of the reaction test apparatus 20 and the collars 72 of the exposure apparatus 22 permits the reaction test apparatus 20 to be comfortably engaged into the exposure apparatus 22.

A biasing arrangement on the upper surface of the fixed shutter 68 resists the downward movement of the reaction test apparatus 20 when it is placed into contact on the top of the fixed shutter 68. The biasing arrangement preferably includes a pair of biasing springs 73, on opposing sides of the upper surface of the fixed shutter 68. The biasing springs 73 are preferably leaf springs, as illustrated, or may be coil springs or any other suitable type. The biasing springs 73 cooperate with other portions of the mechanism in translation of the reaction test apparatus 20 within the exposure apparatus 22, in a manner to be described subsequently.

A movable shutter 74 is slidably disposed below the fixed shutter 68, and can be moved relative to the fixed shutter with an external shutter handle 76. In the preferred embodiment, the movable shutter 76 has a plurality of openings 78 therethrough. The openings 78 have the same pattern and spacing as the openings 70 in the fixed shutter 68, but each of the openings 78 is physically offset from its corresponding opening 70 in the direction of the movement of the movable shutter 74. Consequently, when the movable shutter 74 is closed, the movable shutter 74 blocks the openings 70, and there is no continuous light path through the two shutters 68 and 74. When the movable shutter 74 is opened by grasping the handle 76 and pulling the movable shutter 74 outwardly, at the full extension the openings 78 line up with the openings 70, and there is a line of sight path through the two shutters 68 and 74 at each of the openings 70 and 78. This preferred approach is for a short throw design for the movable shutter 74. Alternatively, the movable shutter can be made a solid piece, requiring that it be withdrawn fully to create a line of sight path.

Within the lower housing 64 below the movable shutter 74 is a piece of photographic film 80, which is exposed to the test wells 28 when the movable shutter 74 is opened to align the openings 70 and 78. Preferably, the film 80 is of the instant developing type, and there is provided an instant processing film pack 82 to accomplish the developing of the film 80. The preferred type of film 80 has an ASA rating of 20,000, which is available in packs of eight instantly processing prints from Polaroid Corporation as its Type 612 film. The film pack 82 is self contained, and need only be inserted into the conforming lower housing 64 with the film 80 below the movable shutter 74.

The upper housing 66 includes a mechanism for applying pressure to the tops of the test wells 28 when the exposure apparatus 22 is closed. An arched rubber diaphragm 84 is positioned above the location of each of the collars 72, as determined when the apparatus 22 is closed, but separated from the collars so that the diaphragms 84 contact and cover the tops of the test wells 28 when the apparatus 22 is closed with a reaction test apparatus 20 in place. The rubber diaphragms 84 are mounted on a diaphragm support 86, which has a pressure bar 88 portion thereof extending through the top of the upper housing 66 through a light-tight seal. The pressure bar 88 is supported on the diaphragm support 86 by rods 130. Coil springs 134 and 136 position the diaphragm support 86 so that the diaphragms 84 are loosely in contact with the tops of the upper reaction cups 30, until an external downward force is applied to the pressure bar 88. The upper spring 134 reacts between the pressure bar 88 and a portion of the housing 66, indicated by numeral 132. The lower spring 136 reacts between the portion of the housing 132 and the diaphragm support 86. The lower spring 136 normally has a higher spring constant than the upper spring 134, to restore the position of the pressure bar 88 after operation is complete.

A downward force applied to the pressure bar 88 against the resistance of the spring 134 brings the diaphragms 84 into close, sealing contact with the tops of the upper reaction cups 30, and continued downward force compresses the air inside the diaphragms 84 and the upper reaction cups 30. A sufficient downward force builds up sufficient pressure within the upper reaction cups 30 to pop out the grease plug 42 from the bottom of the orifice 40, so that liquid in the upper reaction cups 30 can flow through the orifice 40 and into the lower reaction cups 32. Where there is no grease plug 42 because surface tension of the liquid is sufficient to prevent liquid from otherwise flowing through the orifice 40, the downward pressure is sufficient to overcome the surface tension and force the liquid of the test specimen downward through the orifice 40. The diaphragms 84 provide a structurally simple, reliable method for moving the liquid reactants from the upper reaction cup 30 into the lower reaction cup 32.

The luminescent chemical reactions that produce the light recorded on the film 46 produce relatively faint light, and several techniques are utilized to use that light as effectively as possible. The tubular sectioning 46 of the lower reaction cup 32, discussed previously, is one such technique. A very fast film, such as the ASA 20,000 film previously discussed, is typically used. Another technique to utilize the light most fully is to contact the bottom 44 of the lower reaction cup 32 directly to the film 80 during exposure. This can be accomplished by translating the reaction test apparatus 20 downwardly to bring the bottom 44 of the lower reaction into contact with the film 80, after the movable shutter 74 is opened. An externally operable translation mechanism is provided for this purpose.

The translation mechanism includes a rod 92 mounted horizontally through the center of the upper housing 66 and fixed at each end in a bearing surface, so that the rod 92 can be rotated. The rod 92 extends outside of the upper housing 66 through a light-tight baffle, and ends in a translation control lever 94. Inside the upper housing 66, the rod has a cam lobe 96 on each end thereof, positioned over the top of the reaction test apparatus 20. Operation of the lever 94 rotates the cam lobe 96 into contact with the top of the reaction control apparatus 20, and continued rotation forces the reaction control apparatus 20 downwardly toward contact with the top of the fixed shutter 68, against the biasing force of the biasing springs 73. At full operation of the cam lobe 96, the reaction test apparatus 20 is forced downwardly sufficiently far that the bottoms 44 of the lower reaction cups 32 directly contact the film 80. This downward movement of the reaction test apparatus 20 is done only when the movable shutter 74 is opened, so that the lower reaction cups 32 can be contacted to the film 80. It is in this position that the exposure pressure bar 88 is operated and the exposure of the film 80 is completed. After exposure is complete, the lever 94 is operated in the reverse direction to rotate the cam lobe 96 to release the pressure on the reaction control apparatus 20, so that the reaction control apparatus 20 moves upwardly under the influence of the biasing spring 73. With the apparatus 20 in its upward position, the movable shutter 74 can be closed.

As is apparent, the movable shutter 74, lever 94, and pressure bar 88 must be operated in the correct sequence for the exposure of the film to be properly completed. To reduce the chances for operator error, an interlock system has been incorporated into the exposure apparatus 22 to prevent an incorrect sequence of operations. The interlock system is best seen by reference to FIGS. 7-10.

Figure 9:
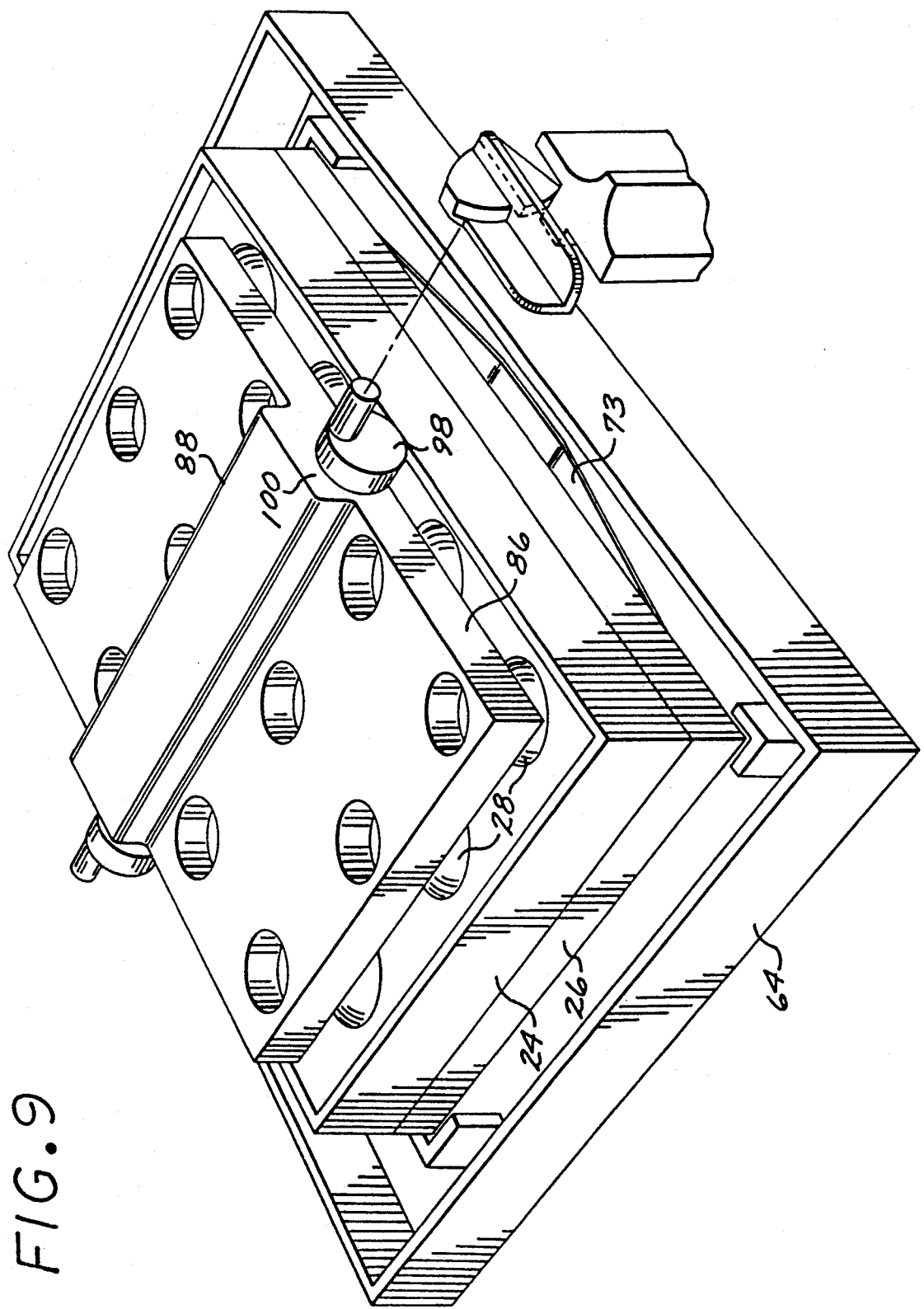
FIG. 9 is a perspective view of the exposure apparatus, with the top cover broken away to illustrate the internal mechanism.

The shutter handle 76 projects from the side of the lower housing 64 in a position to contact a side of the translation control lever 94 in the manner illustrated in FIG. 9. The control lever 94 cannot be rotated to translate the reaction test apparatus 20 downwardly unless the shutter handle is moved to the outward position to align the openings 70 and 78. The shutter handle 76 is attached to the shutter 74, which cannot be moved unless the upper housing 66 is closed to the lower housing 68 to form a light-tight seal therewith, due to an interlock between the two parts. When the shutter handle 76 is operated to open the shutter 74, a notch 110 in the handle 76 engages a tab 112 on the upper housing 66 to lock the upper housing 66 closed, thereby preventing its inadvertant opening at any time at which the film is exposed.

Figure 10:
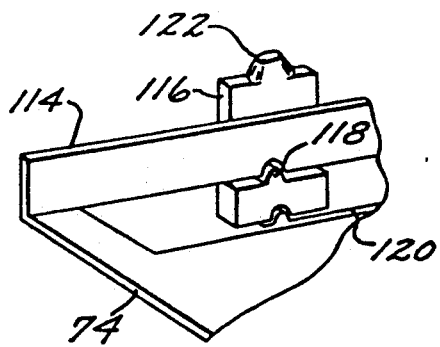
FIG. 10 is a perspective view of a detail of the locking mechanism of the exposure apparatus.

The slide interlock, illustrated in FIG. 10 in a reverse angle view, is effected by a slide lock 116 mounted in the lower housing and biased upwardly by a spring 120. In the locked position illustrated in FIG. 10, a locking tab 118 on the slide lock 116 engages a conforming recess in a locking rail 114 that projects upwardly from one side of the movable shutter 74, preventing movement of the shutter 74. An extension 122 extends upwardly from the top of the slide lock 116, through an opening in the housing 64. The wall of the upper housing 66 depresses the extension 122 when the upper housing 66 is closed, thereby depressing the slide lock 116 against the force of the spring 120 to unlock the shutter 74. As the shutter handle 76 is moved to open the shutter 74 after being so unlocked, the upper housing 66 is locked closed by the engagement between the shutter handle 76 and the tab 112. After the film exposure is complete, the housing 66 can be opened only when the shutter 74 is returned to its closed position by operation of the handle 76, where it is again locked closed by the slide lock 116. This same movement of the handle 76 unlocks the upper housing 66 so that it may be opened, by disengagement of the tab 112.

Mounted on the rod 92 is a pressure bar locking cam 98. The cam 98 is a part-circle cam that contacts the bottom side of the diaphragm support 86 when the translation control lever 94 is in the position that the reaction test apparatus 20 is in its upward position. Thus, in this position, the pressure bar 88 is locked into place and cannot be inadvertently operated. When the translation control lever 94 is operated to force the reaction test apparatus 20 downwardly, the locking cam 98 is rotated away from the diaphragm support 86, and the pressure bar 88 (connected to the diaphragm support 86) can be operated. After exposure of the film 80, the translation control lever 94 is operated to raise the reaction test apparatus 20, again locking the diaphragm support 86 in place. With the translation control lever 94 in this position, the shutter handle 76 can again be operated to close the shutter 74 and unlock the upper housing 66, so that the reaction test apparatus 20 can be opened. This interlock mechanism prevents an incorrect sequence of operations of the external control apparatus.

In the most preferred use, the present invention is used for analysis of the bacteriuria content of urine samples. This test depends upon the reaction of bacterial ATP with luminescent reagents, to produce light that is measured on the film 80. There are two sources of ATP in a urine sample, bacterial and non-bacterial sources. The objective of the preferred bacteriuria test is to measure bacterial sources only. In the preferred test, the ATP in non-bacterial sources is first removed so that it cannot adversely affect the test results, and then the ATP in bacterial sources is released and reacted with the luminescent reagents.

In this test procedure, the upper reaction cup 30 contains a release reactant to lyse somatic cells, releasing non-bacterial ATP therefrom. The release reactant does not affect the bacterial ATP, which remains bound to the bacteria. The release reactant is Triton X100 detergent (polyoxyethylene ether). The upper reaction cup 30 also contains an enzyme elimination reactant (preferably apyrase) to dephosphorolate the non-bacterial ATP to adenosene monophosphate, also known as AMP, which is not measured by the subsequent luminescent assay. The preferred elimination reactant is apyrase enzyme.

To prepare the reagent used in the upper reaction cup 30, about 0.16 units of solid apyrase enzyme and about 100 microliters of 0.2 percent aqueous solution of Triton X100 detergent liquid are mixed with 0.5 milligrams of bovine serum albumin. This mixture is added to the upper reaction cup 30 and freeze dried.

Upon completion of the reaction between the non-bacterial ATP in the urine specimen with the reactants in the upper reaction cup 30, the reacted urine specimen is passed through the orifice 40 into the lower reaction cup 32 for the second reaction. In the lower reaction cup 32, the bacterial ATP is released, and reacted with luminescent reagents. The result is light produced in proportion to the bacterial ATP, with the amount of light measured indicating the amount of bacterial ATP present in the urine specimen.

To prepare the solid material for the lower reaction cup, the following ingredients are mixed together: about 100 microliters of a 0.005 percent to 0.6 percent concentration aqueous solution of a chemical bacterial releasing agent (such as polyoxyethylene ether, hexachlorophene, chlorohexadine, or dimethylsulfoxide), about 10 to 100 micrograms of firefly luciferase enzyme, about 15 micrograms of solid D-luciferin, about 10 microliters of a 10 millimolar magnesium chloride luminescent cofactor, about 0.5 milligrams of bovine serum albumin, and a N-2-Hydroxyethylpiperadine-N'-2-ethanesulfonic acid buffer to bring the pH of the solution to 7.75. The solution is added to the cup 32 and freeze dried.

Urine specimens are then tested in the manner discussed previously. The urine sample is added to the upper reaction cup 30 and reacted therein for a period of time sufficient to eliminate all non-bacterial ATP, which usually requires about 1-10 minutes. The reaction test apparatus 20 is placed into the exposure apparatus 22, the apparatus 22 is closed to form a light-tight enclosure, and the shutter handle 76 is operated to lock the apparatus 22 closed and open the movable shutter 74. With the shutter handle 76 moved to the position with the shutter 74 opened, the interlocked translation control lever 94 is operated to force the reaction test apparatus 20 downwardly and place the bottom 44 of the lower reaction cup 32 in contact with the film 80. At this point, the urine sample is still in the upper reaction cup 30, and there has been no light output. Rotation of the control lever 94 unlocks the diaphragm support 86 and pressure bar 88 in the manner previously described, and the pressure bar 88 can then be operated to press the rubber diaphragms 84 against the tops of the upper reaction cups 30. The pressure thereby created in the upper reaction cup 30 ejects the grease plug 42, so that the liquid in the upper reaction cups 30 flows into the lower reaction cups 32. The liquid mixes with the release reagent and luminescent reagent in the cup 32, producing light in an amount related to the amount of bacterial ATP released. The light is recorded on the film 80. The light producing reaction begins within about 2 seconds or less after operation of the pressure bar 88, and is completed after no more than 30 seconds.

After a sufficiently long time that the light-producing reaction is essentially complete, typically about 30 seconds, the translation control lever 94 is operated to release the downward pressure on the reaction test apparatus 20 so that it moves upwardly to its uppermost travel under the urging of the biasing spring 73. The shutter handle 76 is closed to end the exposure and unlock the upper housing 66. The instant film pack 82 is operated to develop the film 80, either before or after the shutter handle 76 is operated. After the film is developed, typically 60 seconds for Type 612 ASA 20,000 speed instant film, the test results on the film are ready for viewing. The reaction test apparatus 20 (if there are any remaining unused test wells) and exposure apparatus 22 are ready for further testing. The presence of any previously unused test wells 28 of a particular reaction test apparatus 20 is immediately apparent upon visual search for undisrupted portions of the foil cover 48, as the foil cover 48 above used test wells 28 is torn or disrupted during insertion of the specimen into the test well 28.

The present approach for testing provides a mechanically non-complex, inexpensive approach for testing specimens in testing procedures requiring sequential chemical reactions, where the results are to be evaluated by recording the results of a luminescent reaction. Although a particular embodiment of the invention has been described in detail for purposes of illustration, various modifications may be made without departing from the spirit and scope of the invention. Accordingly, the invention is not to be limited except as by the appended claims.

What is claimed is:

1. Luminescence exposure apparatus for conducting luminescence reaction tests on specimens contained within test wells in a reaction test apparatus, comprising:

a lower housing having
        a flat, upwardly facing internal surface comprising means for receiving a piece of light-sensitive film thereupon,
        a mask covering said upwardly facing surface and having a plurality of openings therethrough positioned to correspond to the locations of said test wells in the reaction test apparatus,
        biasing means on said mask for resisting the downward movement of the reaction test apparatus, when the reaction test apparatus is placed upon said mask, and a movable shutter between said internal surface and said mask; and an upper housing including translation means for controllably urging said reaction test apparatus downwardly against the resistance of said biasing means, thereby contacting the bottoms of the reaction wells in the reaction test apparatus with the piece of light-sensitive film in said lower housing, and pressure application means for applying a pressure to the top of the reaction wells in said reaction test apparatus responsive to a force applied externally to said exposure apparatus, said upper housing and said lower housing being configured so as to fit together so as to exclude light from the interior thereof.

2. The exposure apparatus of claim 2, wherein said reaction test apparatus includes a plurality of test wells, each of said test wells including a lower reaction cup having a final reactant therein, an upper reaction cup positioned above said lower reaction cup and having a penultimate reactant therein, said upper reaction cup further having an orifice in the bottom thereof disposed such that liquid flowing through said orifice is discharged into said lower reaction cup;

a support for said test wells and the cups thereof, said support including an upper plate supporting said upper reaction cup, said plates being keyed to register with each other.

3. The exposure apparatus of claim 1, wherein said translation means includes a cam contactable to the reaction test apparatus to urge said reaction test apparatus toward said mask against the resistance of said biasing means, and an external lever connected to said cam and operable to turn said cam.

4. The exposure apparatus of claim 1, wherein said pressure application means includes a rubber diaphragm in the underside of said upper housing and positioned so as to be directly over the top of the test well of the reaction test apparatus, and an externally extending pressure bar attached to said rubber diaphragm, whereby the rubber diaphragm is moved downwardly by an external force applied to said pressure bar, thereby applying pressure to the top of the reaction well contacted by said diaphragm.

5. The exposure apparatus of claim 1, further including locking means for preventing improper operation of said apparatus, said locking means including a movable shutter lock, said movable shutter lock preventing the opening of said movable shutter when said reaction test apparatus is not in contact with the light-sensitive film in said lower housing, and a pressure application means lock, said pressure application means lock preventing the operation of said pressure application means when said reaction test apparatus is not in contact with the light-sensitive film in said lower housing.

6. The exposure apparatus of claim 1, wherein the upper housing is joined to the lower housing with a hinge.

7. The exposure apparatus of claim 1, wherein the piece of film is instantly developing film.

* * * * *